(12) United States Patent
Namii

(10) Patent No.: US 7,507,003 B2
(45) Date of Patent: Mar. 24, 2009

(54) LIGHT COLLECTIVE OPTICAL SYSTEM

(75) Inventor: Yasushi Namii, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 73 days.

(21) Appl. No.: 11/581,092

(22) Filed: Oct. 13, 2006

(65) Prior Publication Data

US 2007/0103912 A1    May 10, 2007

(30) Foreign Application Priority Data

Sep. 9, 2005    (JP)    ............................. 2005-261671

(51) Int. Cl.
*F21V 7/00* (2006.01)
(52) U.S. Cl. ........................ 362/341; 362/268; 362/299; 362/300; 362/327; 362/328
(58) Field of Classification Search ................. 362/341, 362/334–338, 620, 626, 268, 298–302, 304, 362/305, 307, 308, 309, 327, 328, 332, 551, 362/553, 554, 555, 558, 560, 326
See application file for complete search history.

(56) References Cited

U.S. PATENT DOCUMENTS

| | | | | |
|---|---|---|---|---|
| 6,022,123 | A * | 2/2000 | Tomioka et al. | 362/244 |
| 2004/0070855 | A1 * | 4/2004 | Benitez et al. | 359/858 |
| 2006/0285332 | A1 * | 12/2006 | Goon et al. | 362/327 |

FOREIGN PATENT DOCUMENTS

JP        10-048539        2/1998

* cited by examiner

*Primary Examiner*—Ali Alavi
*Assistant Examiner*—Evan Dzierzynski
(74) *Attorney, Agent, or Firm*—Kenyon & Kenyon LLP

(57) ABSTRACT

A light collective optical system includes a single optical member having a first reflecting surface and a second reflecting surface. In this case, the first reflecting surface partly has a first transmissive-refractive surface and the second reflecting surface partly has a second transmissive-refractive surface. The first transmissive-refractive surface and the second transmissive-refractive surface are nearly coaxially arranged. Whereby, it is possible to provide the light collective optical system which is capable of illuminating an object to be illuminated with high illuminance and is compact and a light source device using the light collective optical system.

18 Claims, 15 Drawing Sheets

LIGHT COLLECTIVE OPTICAL SYSTEM

This application claims benefits of Japanese Application No. 2005-261671 filed in Japan on Sep. 9, 2005, the contents of which are hereby incorporated by reference.

BACKGROUND OF THE INVENTION

1. Field of the Invention

This invention relates to a light collective optical system for light sources that has a wide divergence angle, and in particular, to a light collective optical system of a light source device used in an endoscope or a surgical microscope.

2. Description of Related Art

Recently, endoscopes have been widely used in which the internal organs are observed by inserting a slender insertion tube portion into a body or treatment tools inserted into a treatment tool channel are used when the necessity arises and thereby various treatments can be carried out. A conventional light source device used in such an endoscope is constructed so that a reflecting mirror is placed only behind a light source lamp, and direct light from the light source lamp and reflected light by the reflecting mirror are collected at the entrance end face of a light guide. In the conventional light source device, however, since the numerical aperture of the light guide is generally small, part of the direct light from the light source lamp is scattered to impair the efficiency of incidence on the light guide, and it is difficult to efficiently transmit the light from the light source lamp to the light guide.

Thus, in order to obviate such a defect, various light source devices shown in FIGS. 1A-1C are proposed (refer to, for example, Japanese Patent Kokai No. Hei 10-48539). In these figures, reference numeral 1 denotes a light source; 2, 3, 5, 6, and 8 denote reflecting mirrors; 6a denotes an aperture; 4 and 9 denote light guides; and 7 denotes a collective lens.

SUMMARY OF THE INVENTION

The light collective optical system according to the present invention (1) comprises, in order from the light source side, a first transmissive-refractive surface, a second reflecting surface, a first reflecting surface, and a second transmissive-refractive surface which are coaxially arranged along the traveling direction of a light ray.

The light collective optical system according to the present invention (2) is constructed so that in Item (1), the first transmissive-refractive surface and the first reflecting surface are located on the same surface, and the second transmissive-refractive surface and the second reflecting surface are located on the same surface.

The light collective optical system according to the present invention (3) includes a single optical member having a first reflecting surface and a second reflecting surface. In this case, the first reflecting surface partly has the a transmissive-refractive surface, the second reflecting surface partly has a second transmissive-refractive surface, and the first transmissive-refractive surface and the second transmissive-refractive surface are nearly coaxially arranged.

The light collective optical system according to the present invention (4) includes a single optical member having a first reflecting surface and a second reflecting surface. In this case, the first reflecting surface partly has a first transmissive-refractive surface, the second reflecting surface partly has a second transmissive-refractive surface, the first transmissive-refractive surface is placed in the proximity of a bright spot of a light source, light with a narrow divergence angle from the bright spot of the light source passes through the first transmissive-refractive surface and the second transmissive-refractive surface, and light with a wide divergence angle from the bright spot of the light source travels in order of the first transmissive-refractive surface, the second reflecting surface, the first reflecting surface, and the second transmissive-refractive surface so that the image of the bright spot of the light source is projected in the proximity of the second transmissive-refractive surface.

The light collective optical system according to the present invention (5) satisfies the following condition in any one of Items (1), (3), and (4):

$$1 < r2/(n'/(-1/d0-(1-n')/r1)-d1/n') \tag{1}$$

where when $d0=0$, $1 < -r2 \times n'/d1$; $r1$ is the radius of curvature of the first reflecting surface; $r2$ is the radius of curvature of the second reflecting surface; $n'$ is the refractive index of a medium, relative to the d line, between the first transmissive-refractive surface and the second transmissive-refractive surface; $d0$ is a distance from the first transmissive-refractive surface to the bright spot of the light source; and $d1$ is a coaxial distance between the first reflecting surface and the second reflecting surface.

The light collective optical system according to the present invention (6) satisfies the following condition in Item (5):

$$r2/(n'/(-1/d0-(1-n')/r1)-d1/n') < 3 \tag{1'}$$

where when $d0=0$, $-r2 \times n'/d1 < 3$.

The light collective optical system according to the present invention (7) satisfies the following condition in any one of Items (1), (3), and (4):

$$0 < (1/r1+1/r2) \times r2 \tag{2}$$

where $r1$ is the radius of curvature of the first reflecting surface and $r2$ is the radius of curvature of the second reflecting surface. For the sign, the traveling direction of light (the right-hand direction in FIG. 2) is to be positive.

The light collective optical system according to the present invention (8) satisfies the following condition in Item (7):

$$(1/r1+1/r2) \times r2 < 3 \tag{2'}$$

The light collective optical system according to the present invention (9) satisfies the following condition in Item (7) or (8):

$$1 < \beta2/\beta1 \tag{3}$$

where $\beta1$ is the area of an effective range $\alpha1$ of the first transmissive-refractive surface and $\beta2$ is the area of an effective range $\alpha2$ of the second transmissive-refractive surface.

The light collective optical system according to the present invention (10) satisfies the following condition in Item (9):

$$\beta2/\beta1 < 80 \tag{3'}$$

The light collective optical system according to the present invention (11) satisfies the following conditions in Item (10):

$$1 < d1^2/\beta1 < 80 \tag{4}$$

$$1 < \Phi^2/\beta1 < 150 \tag{5}$$

where $d1$ is a coaxial distance between the first reflecting surface and the second reflecting surface and $\Phi$ is the outer diameter of the first reflecting surface.

The light collective optical system according to the present invention (12) is such that in any one of Items (1), (3), and (4), the effective range of each of the first transmissive-refractive surface and the second transmissive-refractive surface has a shape analogous to the bright spot of the light source.

The light collective optical system according to the present invention (13) is such that in any one of Items (1), (3), and (4), the effective range of the first transmissive-refractive surface is larger in size than the bright spot of the light source.

The light collective optical system according to the present invention (14) is such that in any one of Items (1), (3), and (4), at least one of the first reflecting surface and the second reflecting surface is aspherical.

The light source device using the light collective optical system of the present invention (15) comprises a light source; a collective optical system including, in order from the light source side, a first transmissive-refractive surface, a second reflecting surface, a first reflecting surface, and a second transmissive-refractive surface which are coaxially arranged along the traveling direction of a light ray; and a spherical reflecting mirror placed behind the bright spot of the light source so that a light beam diverging backward from a bright spot of the light source is reflected back toward the bright spot of the light source.

The light source device using the light collective optical system of the present invention (16), in Item (15), is one of a halogen lamp, a xenon lamp, and a mercury vapor lamp.

The light source device using the light collective optical system of the present invention (17) comprises a light source which is a light-emitting diode or a laser diode; and a light collective optical system including, in order from the light source side, a first transmissive-refractive surface, a second reflecting surface, a first reflecting surface, and a second transmissive-refractive surface which are coaxially arranged along the traveling direction of a light ray.

The light source device using the light collective optical system of the present invention (18) comprises a collective optical system including, in order from the light source side, a first transmissive-refractive surface, a second reflecting surface, a first reflecting surface, and a second transmissive-refractive surface which are coaxially arranged along the traveling direction of a light ray; and a light guide placed in the proximity of the position of image formation of the bright spot of the light source.

According to the present invention, even in a light source with wide diffusion, it becomes possible to effectively collect light to a propagation means such as the light guide or to brightly illuminate an observation object directly.

These and other features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, the function and effect of the present invention will be explained.

When the present invention is constructed as mentioned in Items (1)-(4), it becomes possible that light with a narrow divergence angle, emitted from the light source, passes through the first transmissive-refractive surface and the second transmissive-refractive surface, while light with a wide divergence angle in which light collection is difficult travels in order of the first transmissive-refractive surface, the second reflecting surface, the first reflecting surface, and the second transmissive-refractive surface and thereby is collected.

Figure 1A:
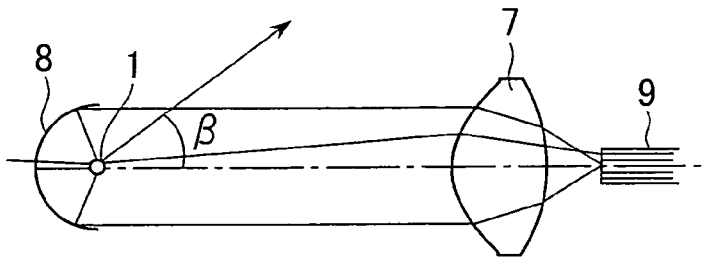
FIGS. 1A, 1B, and 1C are views showing structures of conventional light collective optical systems that are different from one another.
Figure 1B:
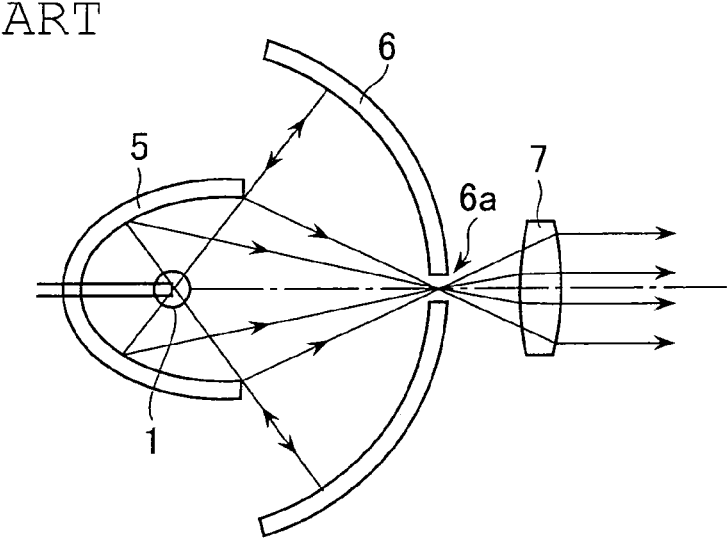
Figure 1C:
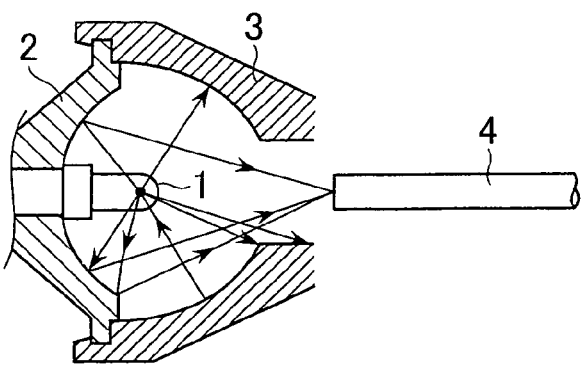
Figure 2:
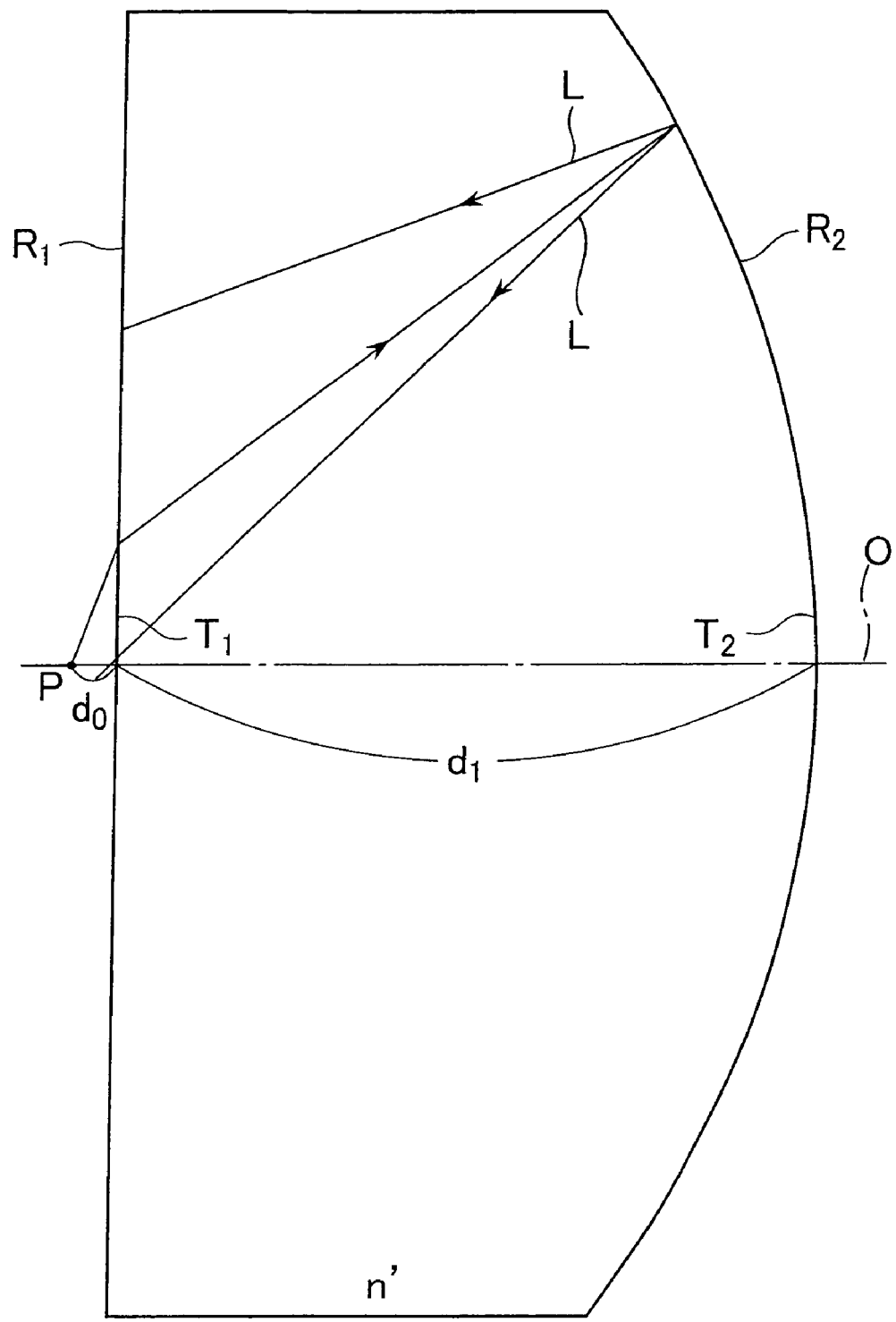
FIG. 2 is an explanatory view of Condition (1) in the present invention.

Subsequently, reference is made to Condition (1) with reference to FIG. 2. Light with a wide divergence angle emitted from the light source travels in order of a first transmissive-refractive surface T1, a second reflecting surface R2, a first reflecting surface R1, and a second transmissive-refractive surface T2. Here, when a light ray is reflected toward the first reflecting surface R1 by the second reflecting surface R2, it is desirable that the light, like a ray L, is reflected toward the first reflecting surface. However, light, like a ray L', traveling toward the first transmissive-refractive surface T1 may be produced, depending on the radius of curvature of the second reflecting surface. The light, like the ray L', traveling toward the first transmissive-refractive surface suffers the loss of the amount of light as a result in such a manner that the light is absorbed in the light source. Thus, a condition for preventing such a loss is introduced.

First, it is said to be good practice that the position of the virtual image of light incident on the second reflecting surface R2 is located within the radius of curvature of the second reflecting surface. For example, when the position of the virtual image of the light incident on the second reflecting surface coincides with the radius of curvature of the second reflecting surface, the light incident on the second reflecting surface is naturally reflected back toward the first transmissive-refractive surface. As such, when the radius of curvature of the second reflecting surface is increased, the light, like the ray L, is reflected toward the first reflecting surface R1. When the refractive index of an optical member shown in FIG. 2 is represented by n', a distance between a light source P and the first transmissive-refractive surface T1 by d0, the radius of curvature of the first reflecting surface R1 by r1, and a distance, measured along an optical axis O, between the first transmissive-refractive surface T1 and the second transmissive-refractive surface T2 by d1, the position of the virtual image of the light incident on the second reflecting surface R2 is as shown below.

Figure 3:
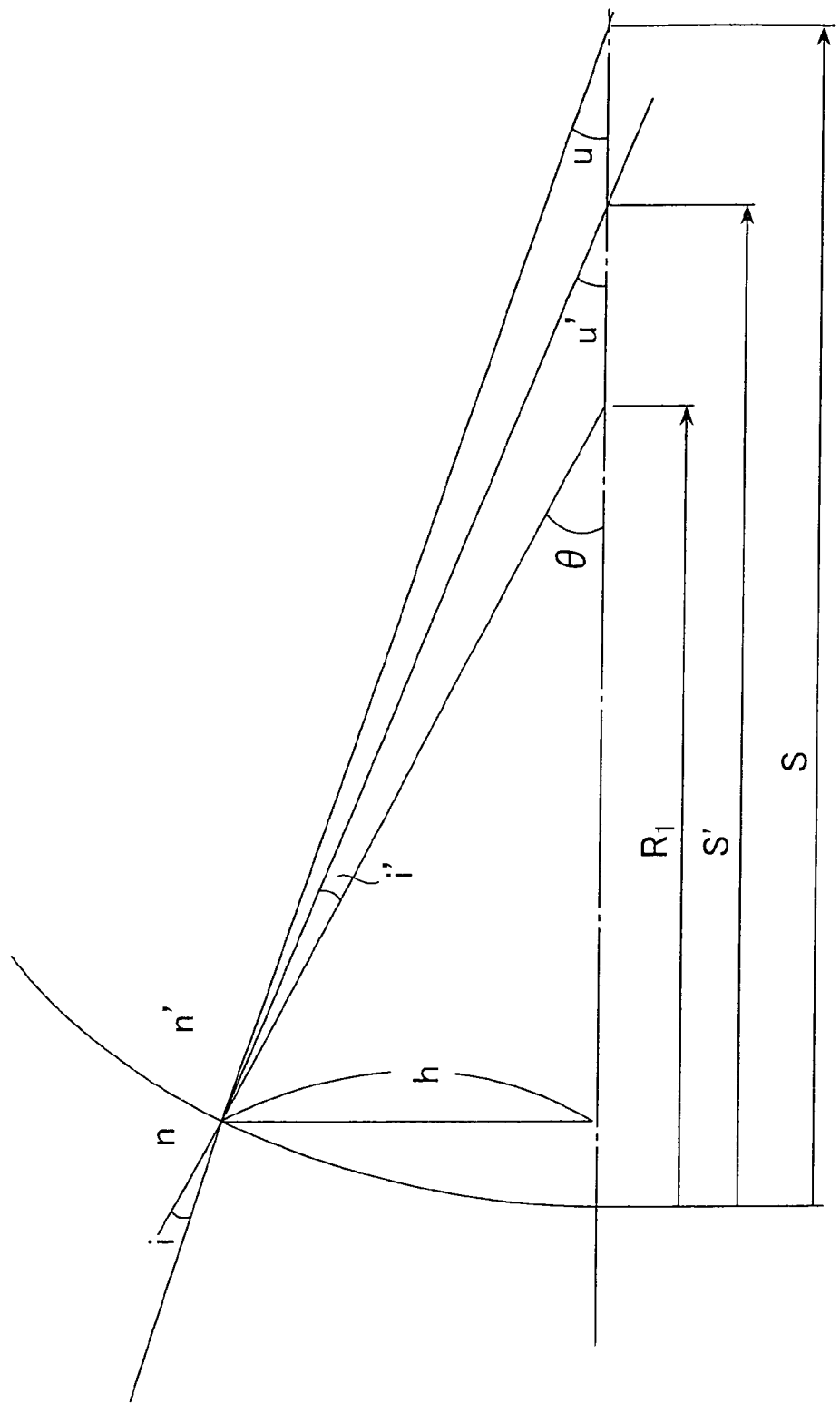
FIG. 3 is another explanatory view of Condition (1) in the present invention.

From properties of paraxial rays shown in FIG. 3: $\theta=h/r1$, $u=h/S$, $u'=h/S'$, $ni=n'i'$ (Snell's law), $i=\theta-u$, and $i'=\theta-u'$, a formula, $n(1/r1-1/S)=n'(1/r1-1/S')$, is established. Finding the distance S' from this formula as $n=1$ (air), a formula, $S'=n'/(1/S-(1-n')/r1)$, is obtained. Here, the signs of the distance S of FIG. 3 and the distance d0 of FIG. 2 are opposite to each other, and thus $S'=n'/(-1/d0-(1-n')/r1)$. However, when $d0=0$, the denominator of this formula becomes infinite and as a result, $S'=0$. When the difference between d1/n' and S' is smaller than the radius of curvature r2 of the second reflecting surface R2, as mentioned above, light is not reflected back toward the first transmissive-refractive surface. Thus, a condition for making the light to be not reflected back toward the first transmissive-refractive surface is expressed by $d1/n'-S'<-r2$. However, for the sign, the traveling direction of light (the right-hand direction in FIG. 2 or 3) is to be positive. From the above condition, $$1 < r2/(n'/(-1/d0-(1-n')/r1)-d1/n') \tag{1}$$

where when $d0=0$, $1<-r2\times n'/d1$.

By satisfying this condition, light reflected by the second reflecting surface is reflected by the first reflecting surface without returning to the first transmissive-refractive surface and can be effectively collected.

Figure 4:
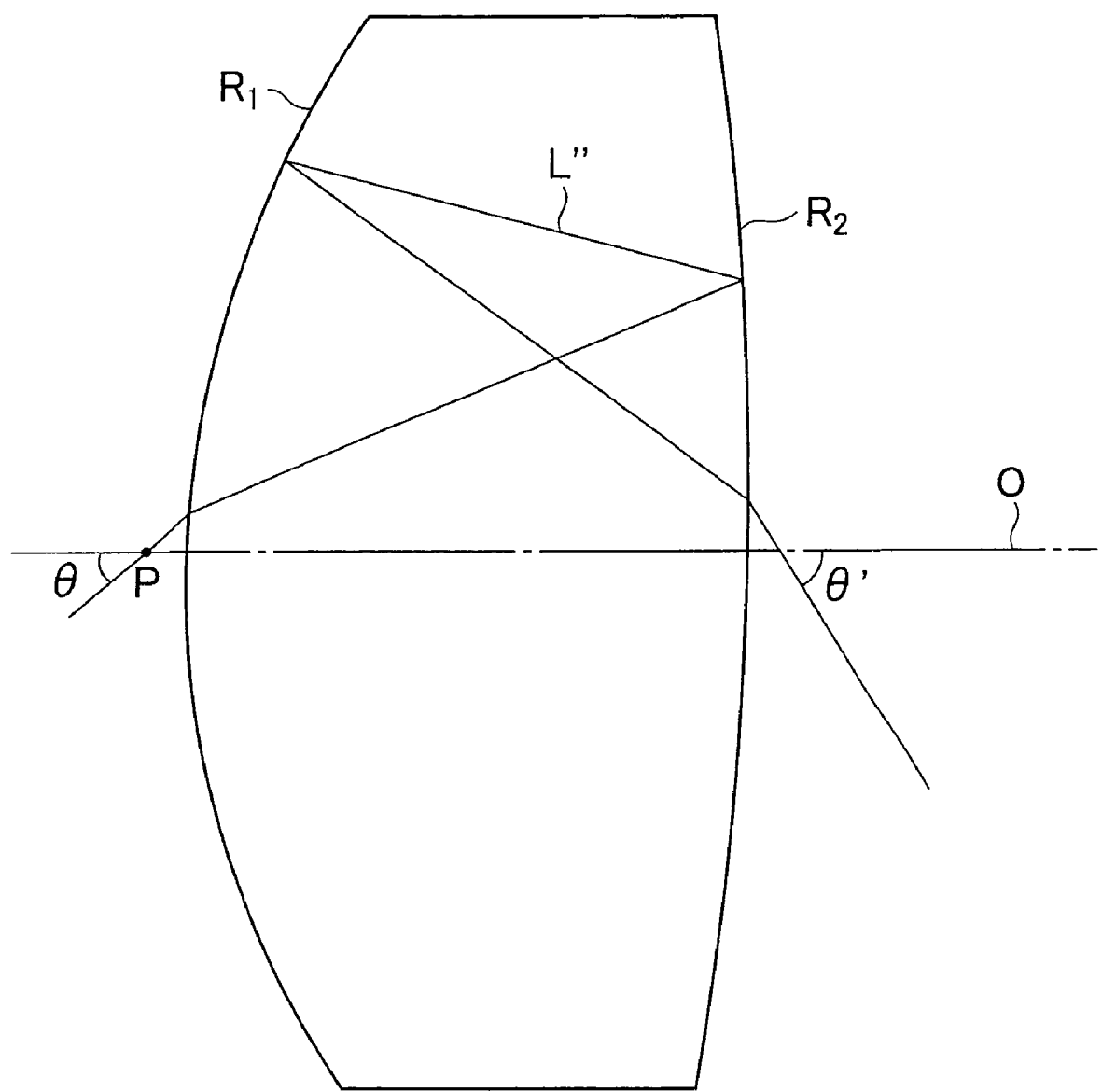
FIG. 4 is an explanatory view of Condition (1') in the present invention.

Even when the radius of curvature of the second reflecting surface R2 is too large with respect to the position of the virtual image of light incident on the second reflecting surface, light from the light source ceases to be effectively collectable. For example, if a light ray incident on the second reflecting surface R2, as shown in FIG. 4, is reflected like a ray L" by the second reflecting surface R2, light must be made to emerge at a larger angle $\theta'$ than the angle of incidence $\theta$ of light from the light source when an attempt is made to collect the light by the first reflecting surface R1. This reverses the fact that light with a wide divergence angle from the light source is changed to light with a narrow divergence angle by a lens function, and means that the light is made inefficiently incident on the light guide.

Figure 5A:
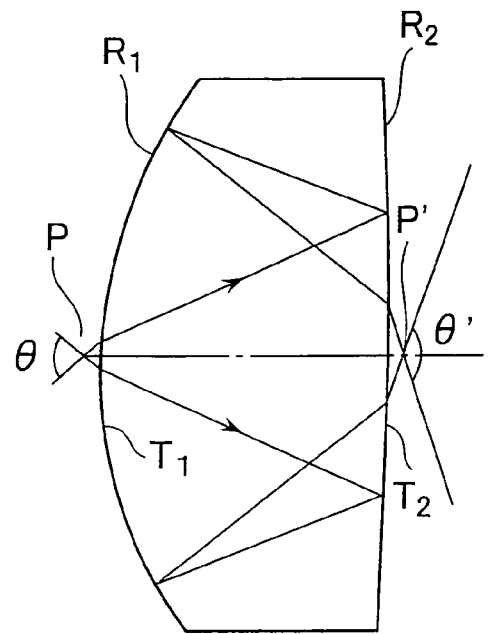
FIGS. 5A and 5B are views for explaining Condition (2) in the present invention.
Figure 5B:
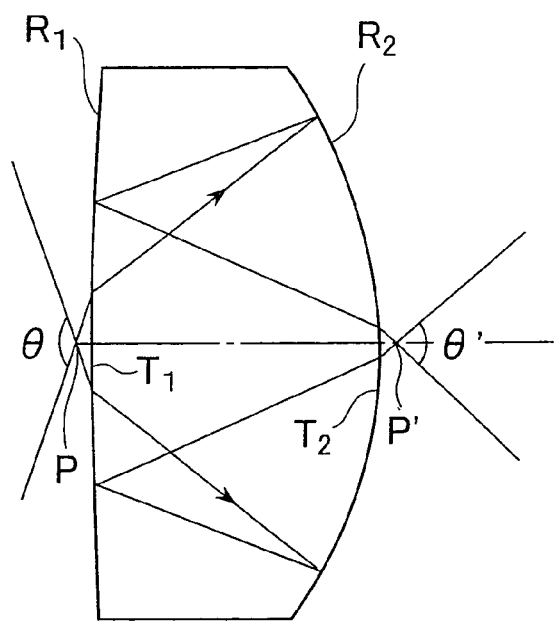

In the endoscope or the microscope, to efficiently transmit light with a wide divergence angle emitted from a small bright spot of the light source to the light guide with a small numerical aperture, it is most efficient to collect light so that the divergence angle of the bright spot of the light source is matched with the small numerical aperture of the light guide. In order to do so, it is necessary to satisfy the above condition. Using FIGS. 5A and 5B, reference is made to this condition. FIG. 5A shows schematically the sectional view of the light collective optical system in the case where the condition is not satisfied. FIG. 5B shows schematically the sectional view of the light collective optical system in the case where the condition is satisfied. Light diverging from a bright spot P of the light source is reflected by the second reflecting surface R2, travels toward the first reflecting surface R1, is reflected by the first reflecting surface R1, and emerges. In this case, when the divergence angle of light diverging from the light source is denoted by $\theta$ and the angle of light collection where the light reaches a point P' is denoted by $\theta'$, it is clear from the figures that $\theta<\theta'$ in FIG. 5A and $\theta>\theta'$ in FIG. 5B. In this way, it becomes possible that light is projected at the narrow divergence angle by the lens function and is made incident on the light propagation member such as the light guide and thereby bright light is efficiently propagated. In order to efficiently project the bright spot of the light source on the light guide, it is desirable that the power of the second reflecting surface is larger than that of the first reflecting surface.

If the upper limit of Condition (2') is exceeded, the power of the second reflecting surface becomes too large with respect to the power of the first reflecting surface. As a result, aberration is produced and light collective optical performance is impaired.

A change from light with a wide divergence angle to light with a narrow divergence angle means that the image of the bright spot of the light source is magnified by the lens function. Thus, it becomes possible that the image of the bright spot of the light source is projected at the magnification more than 1× to thereby make the light efficiently incident on the light guide while reducing and the divergence angle of the bright spot. By satisfying Condition (3), it is possible that the magnification by the first reflecting surface R1 and the second reflecting surface R2 becomes more than 1×.

The light from the bright spot of the light source is transmitted though the first transmissive-refractive surface T1 and is projected in the proximity of the point P' in FIG. 5B (namely, of the second transmissive-refractive surface T2) by the second reflecting surface R2 and the first reflecting surface R1. Since the magnification is more than 1×, the image of the bright spot of the light source is magnified and projected. In the effective range $\alpha 1$ of the first transmissive-refractive surface T1 and the effective range $\alpha 2$ of the second transmission-refraction T2, therefore, unless the effective range $\alpha 2$ is wider, the image of the bright spot of the light source will be eclipsed and will cease to be efficiently projected.

Beyond the upper limit of Condition (3'), light beams traveling directly from the effective range $\alpha 1$ of the first transmissive-refractive surface to the effective range $\alpha 2$ of the second transmissive-refractive surface are increased, which is inefficient.

Below the lower limit of Condition (4), a lens thickness is decreased and light cannot be efficiently collected. Beyond the upper limit, the lens thickness becomes large and a very bulky light collective optical system is obtained, which causes oversizing. Below the lower limit of Condition (5), the effective diameter of the first reflecting surface vanishes and light cannot be reflected by the first reflecting surface. Beyond the upper limit, the outer diameter of the light collective optical system is enlarged and oversizing is caused.

The embodiments will be described below. In each of the embodiments, r1 denotes the radius of curvature of the first reflecting surface, r2 denotes the radius of curvature of the second reflecting surface, n' denotes the refractive index of a medium between the first transmissive-refractive surface and the second transmissive-refractive surface at the d line, d0 denotes a distance between the first reflecting surface and the bright spot of the light source, d1 denotes a coaxial distance between the first reflecting surface and the second reflecting surface, $\alpha 1$ denotes the effective range of the first transmissive-refractive surface, $\beta 1$ denotes the area of the effective range of the first transmissive-refractive surface, $\alpha 2$ denotes the effective range of the second transmissive-refractive surface, $\beta 2$ denotes the area of the effective range of the second transmissive-refractive surface, and $\Phi$ denotes the outer diameter of the first reflecting surface or the second reflecting surface.

Also, in the orthogonal coordinate systems where Z is taken in the direction of the optical axis as an original point at the vertex of the surface, when the radius of curvature at the vertex is represented by r, the conic constant is represented by K, and aspherical coefficients are represented by C4, C6, C8, C10, and C12, the configuration of an aspherical surface of each of the fourth to sixth embodiments is expressed by the following equation:

$$Z = h^2/r(1+\sqrt{(1-(1+K)h/r^2)}) + C4h^4 + C6h^6 + C8h^8 + C10h^{10} + C12h^{12}$$

where $h = \sqrt{(X^2+Y^2)}$

First Embodiment

Lens data of the first embodiment are shown below.
(Light source) d0=0.2
r1=33.3333 d1=5.71 n'=1.51633 (S-BSL7)
r2=−8.55556
α1=3 (dia.), β1=2.25π, α2=5 (dia.), β2=6.25π, Φ=9.5

$$r2/(n'/(-1/d0-(1-n')/r1)-d1/n')=2.1 \quad (1)$$

$$(1/r1+1/r2) \times r2=0.74 \quad (2)$$

$$\beta2/\beta1=2.8 \quad (3)$$

$$d1^2/\beta1=3.6 \quad (4)$$

$$\Phi^2/\beta1=3.2 \quad (5)$$

Figure 6:
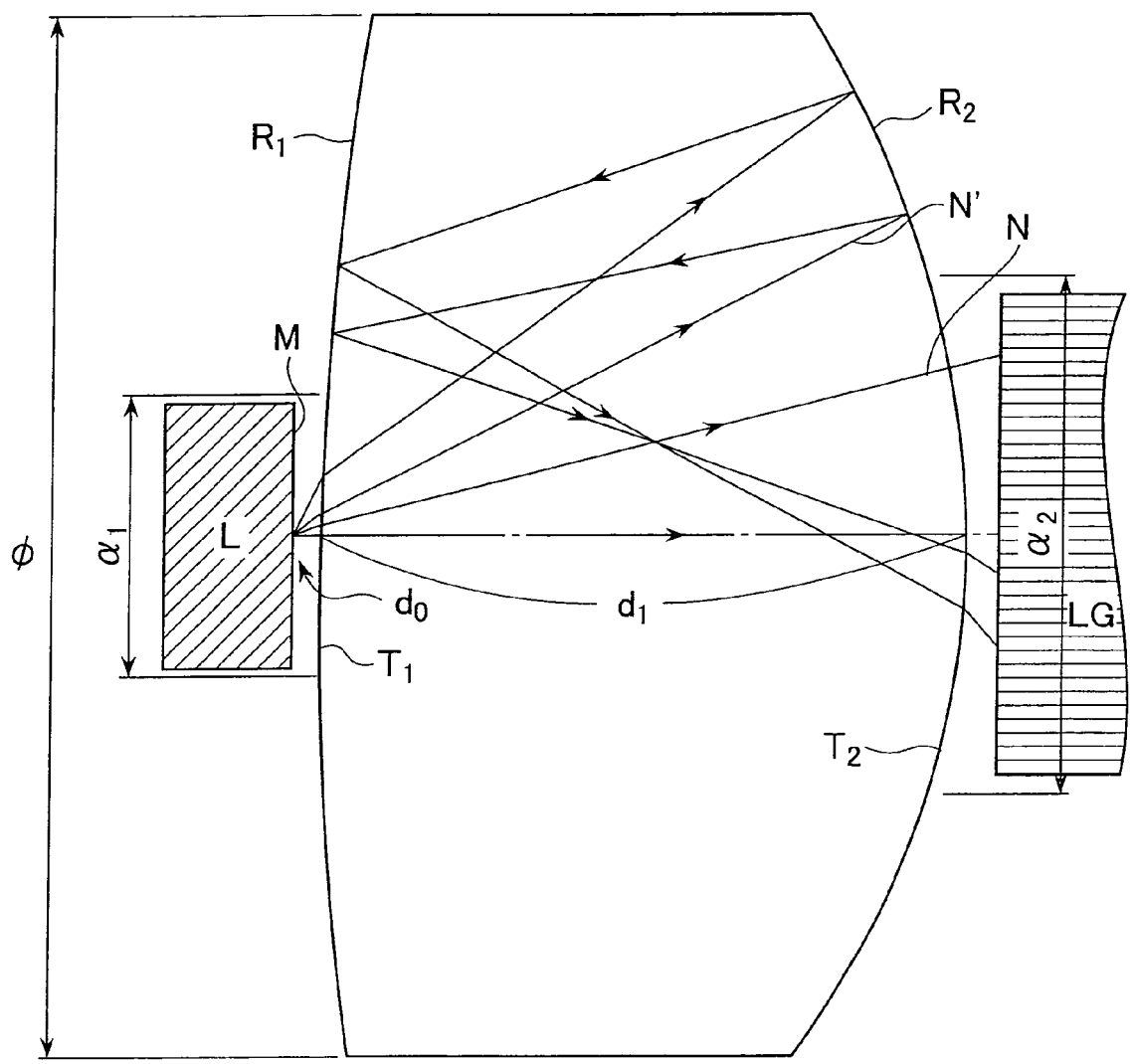
FIG. 6 is a sectional view showing the lens of the light collective optical system of a first embodiment in the present invention.

FIG. 6 shows the sectional view of the light collective optical system of the first embodiment.

The first transmissive-refractive surface T1 and the first reflecting surface R1 are situated on the same surface, and the inside and the outside of the effective range α1 are the first transmissive-refractive surface T1 and the first reflecting surface R1, respectively. The second transmissive-refractive surface T2 and the second reflecting surface R2 are situated on the same surface, and the inside and the outside of the effective range α2 are the second transmissive-refractive surface T2 and the second reflecting surface R2, respectively. A region sandwiched between the first transmissive-refractive surface T1 (the first reflecting surface R1) and the second transmissive-refractive surface T2 (the second reflecting surface R2) is filled with glass. In this figure, reference symbol L denotes an LED light source, M denotes the light-emitting surface of the LED light source, and LG denotes a light guide.

Of light diverging from the light-emitting surface M of the LED light source L, light with a narrow divergence angle passes through the first transmissive-refractive surface T1 and the second transmissive-refractive surface T2 and, like a ray N, is incident on the light guide LG. On the other hand, light with a wide divergence angle, like a ray N', passes through the first transmissive-refractive surface T1, is reflected by the second reflecting surface R2 and the first reflecting surface R1, passes through the second transmissive-refractive surface T2, and is incident on the light guide LG. In this case, the image of the bright spot of the light-emitting surface M of the LED light source is formed close to the second transmissive-refractive surface T2. The light incident on the light guide LG is propagated through the light guide to the distal end of an endoscope not shown in the figure and emerges as the illumination light of the endoscope. By this construction, it becomes possible to efficiently transmit the light with a wide divergence angle of the LED light source to the light guide without any loss.

The first transmissive-refractive surface T1 and the first reflecting surface R1 are situated on the same surface, the second transmissive-refractive surface T2 and the second reflecting surface R2 are situated on the same surface, and the first transmissive-refractive surface T1, the first reflecting surface R1, the second transmissive-refractive surface T2, and the second reflecting surface R2 are constructed of the same optical member. Whereby, since the light with a wide divergence angle from the LED light source can be collected by a single optical member, the adjustment of the reflecting surface on assembly is unnecessary, time required for the assembly can be reduced, and an assembly adjusting mechanism is also unnecessary.

It is needless to say that the light collective optical system of this embodiment can be applied not only to the endoscope, but also to a surgical microscope or anything light is propagated by the light guide.

Second Embodiment

Lens data of the second embodiment are shown below.
(Light source) d0=0.2
r1=−70 d1=20.545 n'=1.51633 (S-BSL7)
r2=−26.1
α1=3 (dia.), β1=2.25π, α2=6 (dia.), β2=9π, Φ=34

$$r2/(n'/(-1/d0-(1-n')/r1)-d1/n')=1.88 \quad (1)$$

$$(1/r1+1/r2) \times r2=1.37 \quad (2)$$

$$\beta2/\beta1=4 \quad (3)$$

$$d1^2/\beta1=46.9 \quad (4)$$

$$\Phi^2/\beta1=40.9 \quad (5)$$

Figure 7:
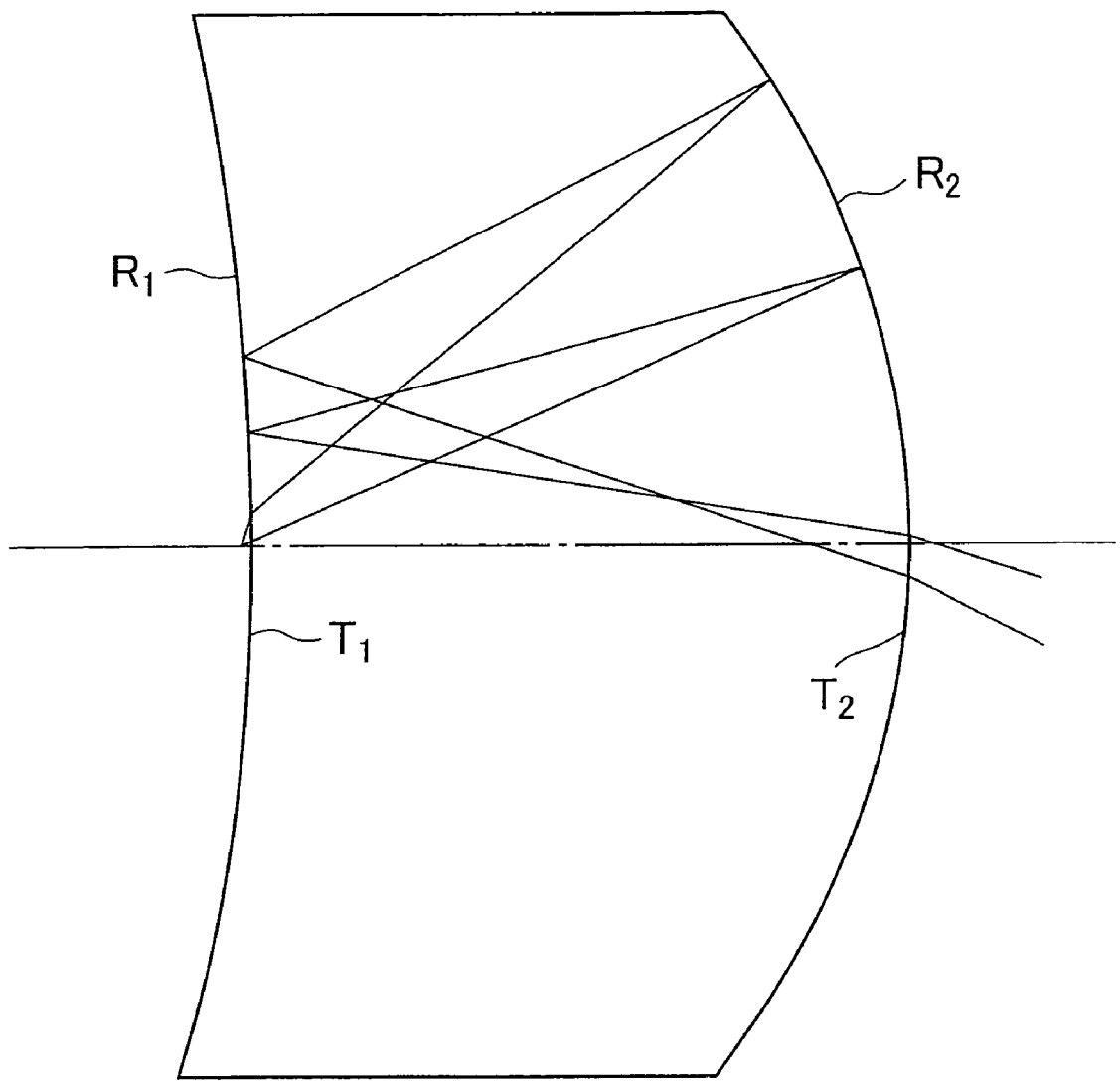
FIG. 7 is a sectional view showing the lens of the light collective optical system of a second embodiment in the present invention.

FIG. 7 shows the sectional view of the collective lens of the second embodiment.

This embodiment, in contrast with the first embodiment, is designed so that the first reflecting surface R1 and the second reflecting surface R2 are modified, the image of the bright spot of the LED light source formed close to the second transmissive-refractive surface T2 is magnified and projected, and light emerges at a narrower distribution angle and is made incident on the light guide (not shown). In general, as the numerical aperture of the light guide is small, the transmittance becomes high and light is propagated without loss. Thus, in the case where the light guide smaller in numerical aperture than that of first embodiment is used, when the light collective optical system of the second embodiment is employed, it becomes possible to propagate light without loss of the amount of light.

Third Embodiment

Lens data of the third embodiment are shown below.
(Light source) d0=0.2
r1=−50 d1=20.545 n'=1.51633 (S-BSL7)
r2=−25.5
α1=3 (dia.), β1=2.25π, α2=7 (dia.), β2=9π, Φ=34

$$r2/(n'/(-1/d0-(1-n')/r1)-d1/n')=1.84 \quad (1)$$

$$(1/r1+1/r2) \times r2=1.51 \quad (2)$$

$$\beta2/\beta1=5.4 \quad (3)$$

$$d1^2/\beta1=46.9 \quad (4)$$

$$\Phi^2/\beta1=40.9 \quad (5)$$

Figure 8:
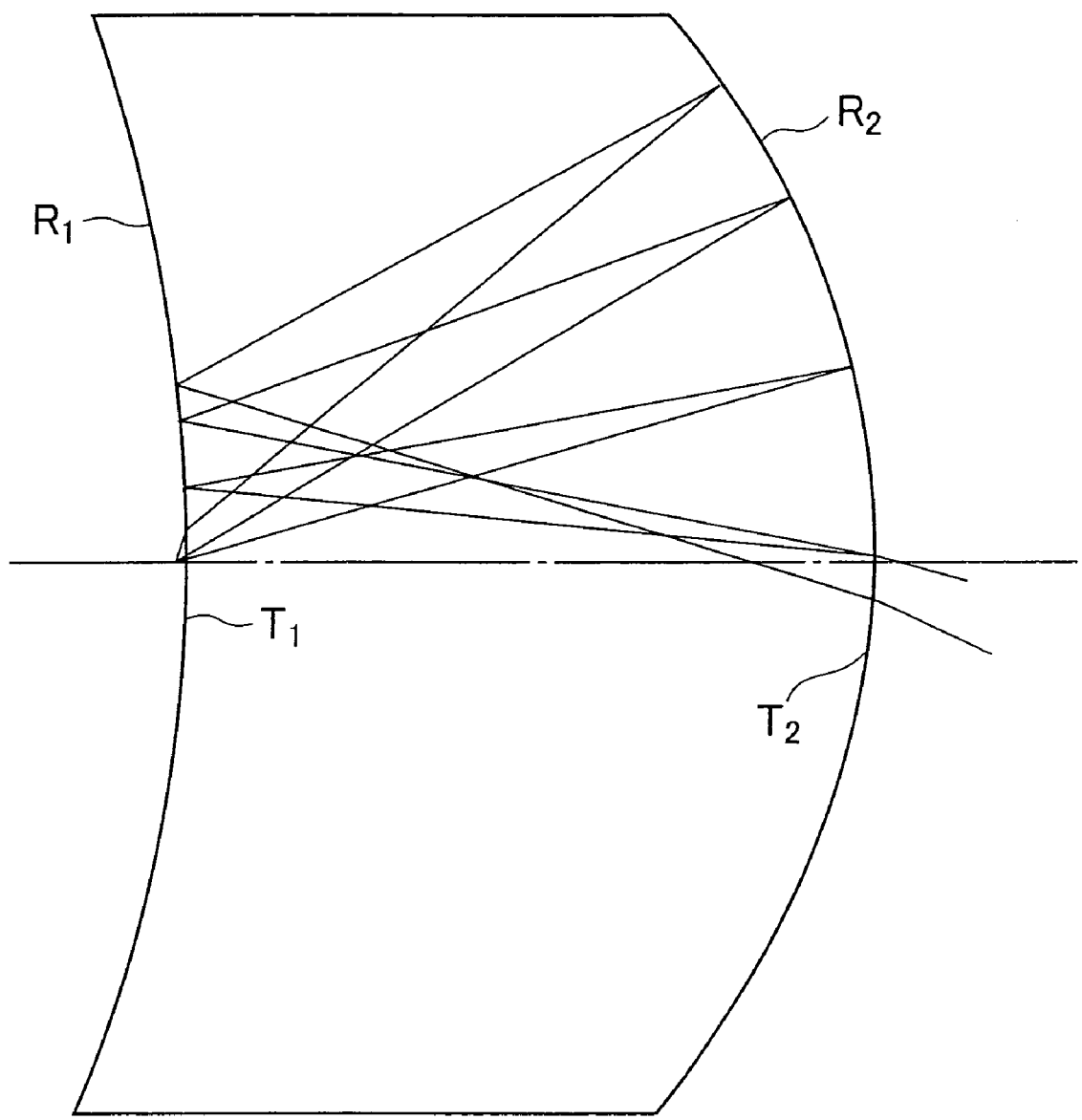
FIG. 8 is a sectional view showing the lens of the light collective optical system of a third embodiment in the present invention.

FIG. 8 shows the sectional view of the collective lens of the third embodiment. This embodiment is constructed so that the numerical aperture is smaller (the angle of emergence is smaller) than that of the second embodiment.

Fourth Embodiment

Lens data of the fourth embodiment are shown below.
(Light source) d0=0.2
r1=∞ d1=10.5 n'=1.51633 (S-BSL7)
r2=−14.4 (aspherical surface)
C6=−2.0×10$^{-7}$, C12=−2.0×10$^{-13}$
α1=3, β1=2.25π, α2=5, β2=6.25π, Φ=17

$$r2/(n'/(-1/d0-(1-n')/r1)-d1/n')=1.99 \quad (1)$$

$$(1/r1+1/r2)\times r2=1 \quad (2)$$

$$\beta2/\beta1=2.8 \quad (3)$$

$$d1^2/\beta1=12.3 \quad (4)$$

$$\Phi^2/\beta1=10.2 \quad (5)$$

Figure 9:
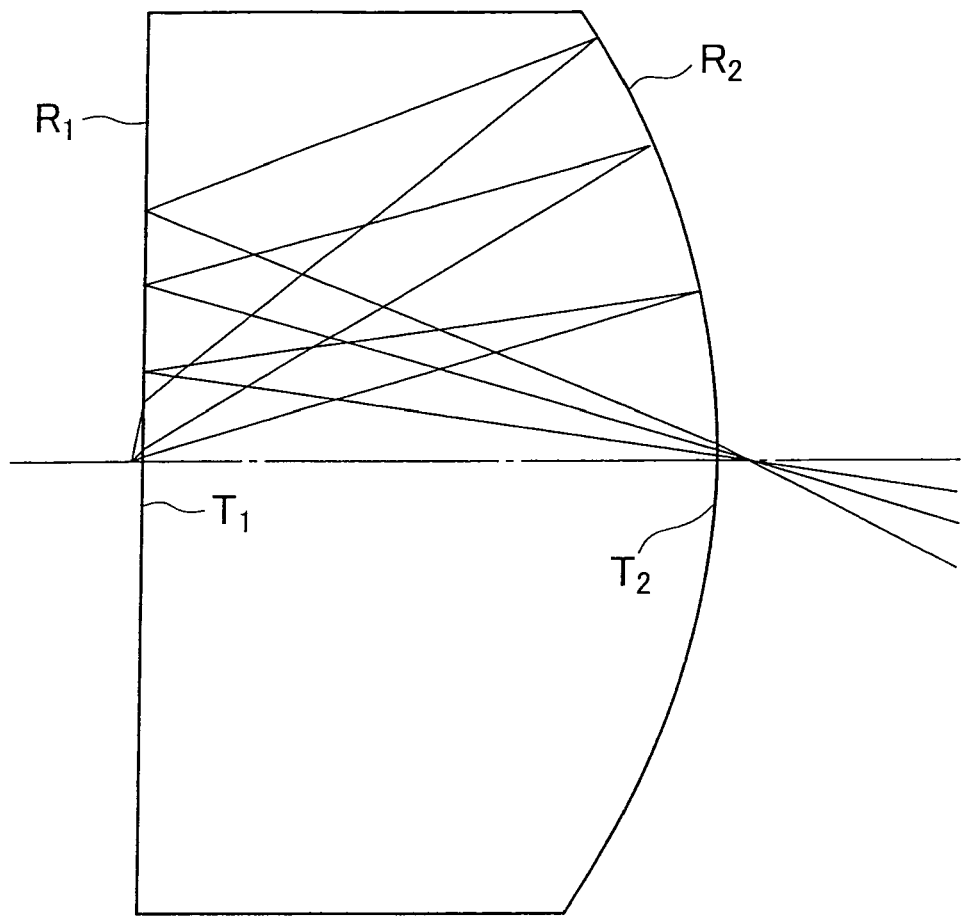
FIG. 9 is a sectional view showing the lens of the light collective optical system of a fourth embodiment in the present invention.

FIG. 9 shows the sectional view of the collective lens of the fourth embodiment. In this embodiment, the second reflecting surface R2 (the second transmissive-refractive surface T2) is configured as an aspherical surface. By adopting the aspherical surface, light can be more efficiently collected to the light guide than in the first embodiment. The first reflecting surface R1 (the first transmissive-refractive surface T1) is flat.

Fifth Embodiment

Lens data of the fifth embodiment are shown below.
(Light source) d0=0.1
r1=50 d1=10.27 n'=1.51633 (S-BSL7)
r2=−15.4 (aspherical surface)
C6=2.24×10$^{-7}$, C12=1.049×10$^{-20}$
α1=3 (dia.), β1=2.25π, α2=6 (dia.), β2=9π, Φ=16

$$r2/(n'/(-1/d0-(1-n')/r1)-d1/n')=2.22 \quad (1)$$

$$(1/r1+1/r2)\times r2=0.69 \quad (2)$$

$$\beta2/\beta1=4 \quad (3)$$

$$d1^2/\beta1=11.7 \quad (4)$$

$$\Phi^2/\beta1=9.1 \quad (5)$$

Figure 10:
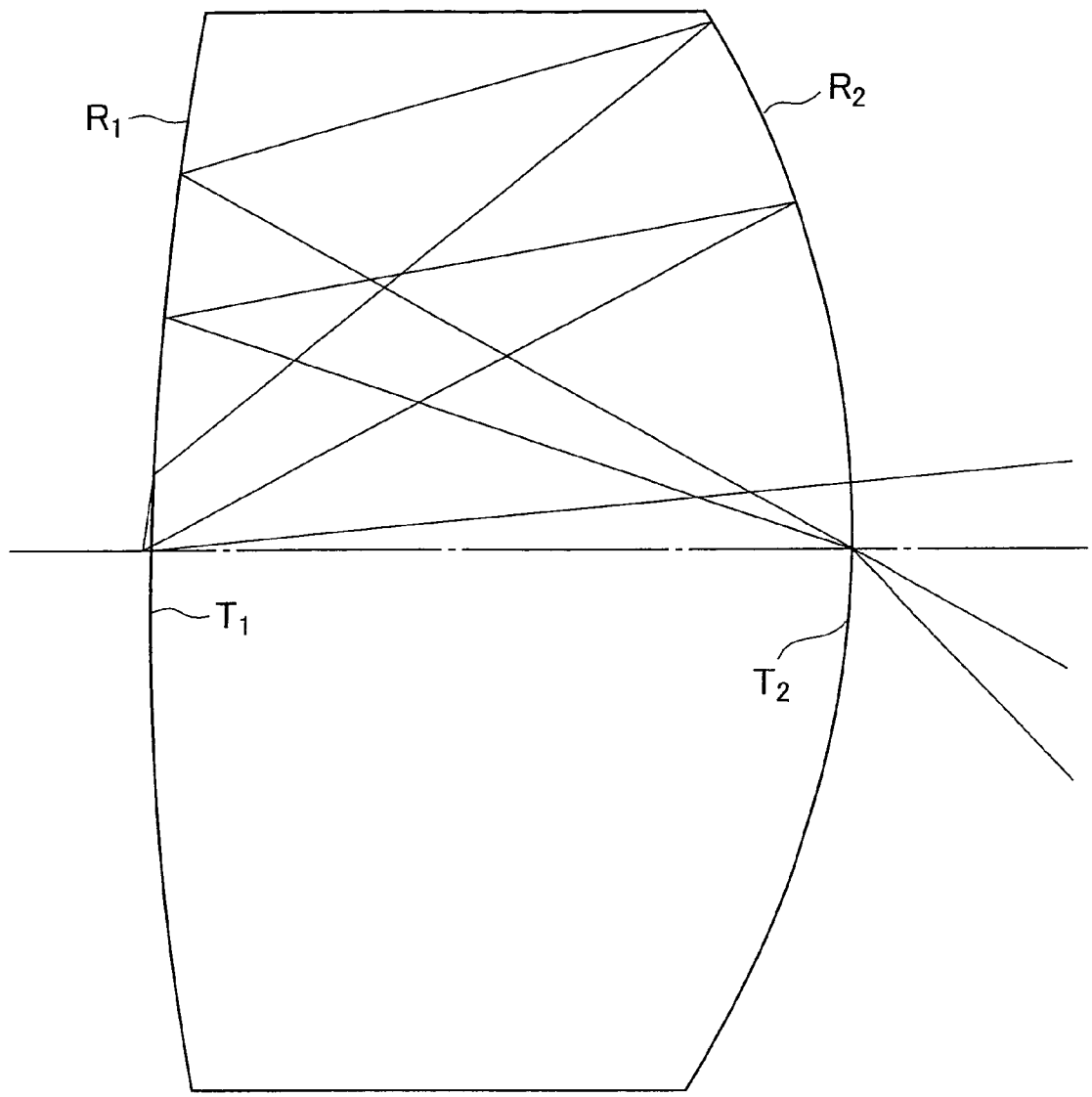
FIG. 10 is a sectional view showing the lens of the light collective optical system of a fifth embodiment in the present invention.

FIG. 10 shows the sectional view of the collective lens of the fifth embodiment. In this embodiment, like the fourth embodiment, the second reflecting surface R2 (the second transmissive-refractive surface T2) is configured as the aspherical surface.

Sixth Embodiment

Lens data of the sixth embodiment are shown below.
(Light source) d0=0.1
r1=∞ d1=14.583 n'=1.51633 (S-BSL7)
r2=−20 d2=12.117
r3=35 d3=11.9 n'=1.51633 (S-BSL7)
r4=−13 (aspherical surface)
C4=−5.4664723×10$^{-5}$, C6=3.7186886×10$^{-7}$, C8=−4.6483608×10$^{-9}$, C10=1.8×10$^{-11}$, C12=−1.5×10$^{-13}$
α1=3, β1=2.25π, α2=5, β2=6.25π, Φ=25

$$r2/(n'/(-1/d0-(1-n')/r1)-d1/n')=2.05 \quad (1)$$

$$(1/r1+1/r2)\times r2=1 \quad (2)$$

$$\beta2/\beta1=2.8 \quad (3)$$

$$d1^2/\beta1=23.6 \quad (4)$$

$$\Phi^2/\beta1=22.1 \quad (5)$$

The sixth embodiment is different from the first to fifth embodiments in which light is made incident on the light guide by the light collective optical system of the present invention, and is an example where the illumination optical system of the surgical microscope is constructed by combining the light collective optical system with another lens.

Figure 11:
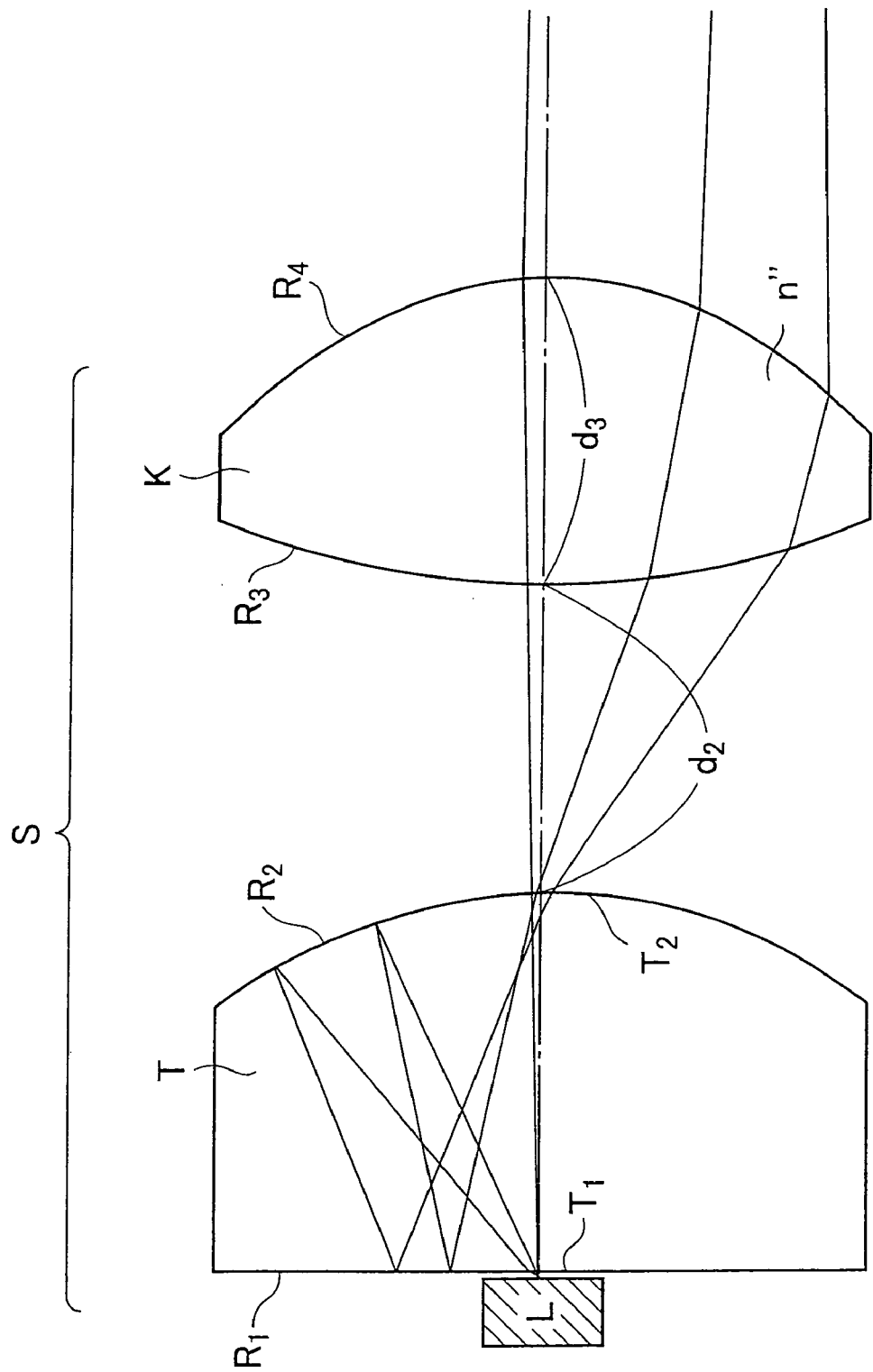
FIG. 11 is a sectional view showing the lens of the light collective optical system of a sixth embodiment in the present invention.

FIG. 11 shows the sectional view of the illumination optical system of this embodiment. An illumination optical system S is constructed so that a lens K is placed on the exit side of a light collective optical system T. In the lens data mentioned above, r3 denotes the radius of curvature of an entrance-side surface R3 of the lens K, r4 denotes the radius of curvature of an exit-side surface R4 of the lens K, d2 denotes a distance between the second reflecting surface R2 (the second transmissive-refractive surface T2) of the light collective optical system and the entrance-side surface R3 of the lens K, d3 denotes the thickness of the lens K, and n" denotes the refractive index of the medium of the lens K at the d line. The exit-side surface R4 of the lens K is aspherical. Light emitted from the LED light source L is incident on the light collective optical system T, follows the same course as in the first to fifth embodiments, and is imaged in the proximity of the second transmissive-refractive surface to form the image of the bright spot of the LED light source. After that, the light enters the lens K, the distribution angle is changed by the function of the lens K, and the light emerges.

Figure 12A:
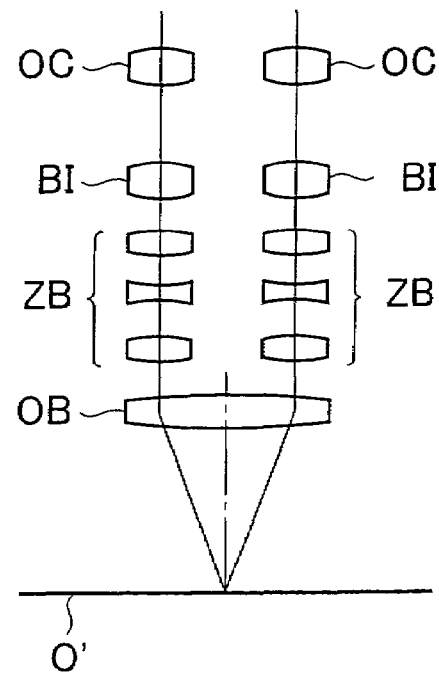
FIGS. 12A and 12B are views showing the optical system of a surgical microscope of the sixth embodiment.
Figure 12B:
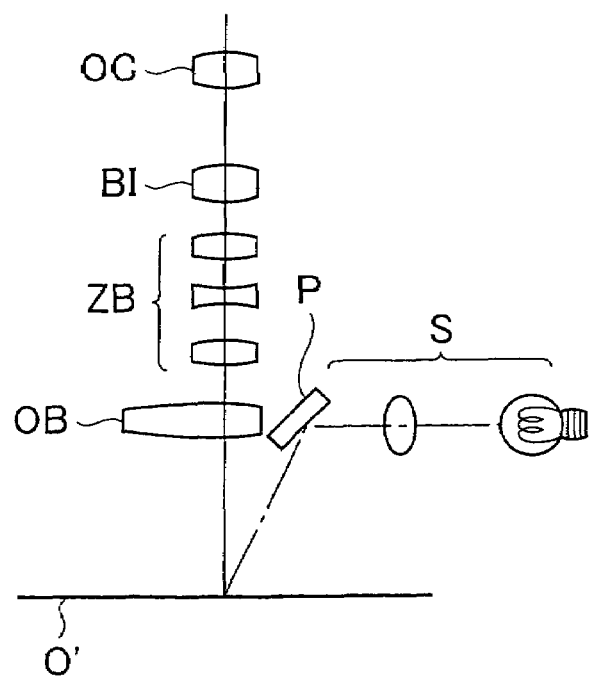

FIGS. 12A and 12B illustrate the optical system of the surgical microscope applying the illumination optical system of the sixth embodiment. FIG. 12A is a front view thereof and FIG. 12B is a side view. An observation object O' is illuminated by the illumination optical system S and a reflecting mirror P, and an viewer observes the object through an objective lens OB, zoom lenses ZB, image-forming lenses BI, and eyepieces OC. Although in this embodiment the reflecting mirror P is placed on the exit side of the lens K, it may be interposed between the lens T and the lens K.

Since the sixth embodiment does not use a transmission means such as the light guide shown in other embodiments, it becomes possible to illuminate the observation object O' without loss of the amount of light. Also, in the sixth embodiment, the LED light source is used and thus is very darker than a high-luminance light source such as a xenon lamp. For the surgical microscope to which the sixth embodiment is applied, therefore, an electronic image microscope in which an image of an object is picked up and displayed as an electronic image is more suitable than an optical microscope in which the object is visually observed.

Seventh Embodiment

Lens data of the seventh embodiment are shown below.
rm=20 dm=20
(Light source) d0=0.2
r1=50 d1=20.545 n'=1.51633 (S-BSL7)
r2=−38
α1=3 (dia.), β1=2.25π, α2=6 (dia.), β2=9π, Φ=34

$$r2/(n'/(-1/d0-(1-n')/r1)-d1/n')=2.74 \quad (1)$$

$$(1/r1+1/r2)\times r2=0.24 \quad (2)$$

$$\beta2/\beta1=4 \quad (3)$$

$d1^2/\beta1=46.9$ (4)

$\Phi^2/\beta1=40.9$ (5)

Here, rm stands for the radius of curvature of a spherical reflecting mirror and dm stands for a distance between the spherical reflecting mirror and the bright spot of the light source.

Figure 13:
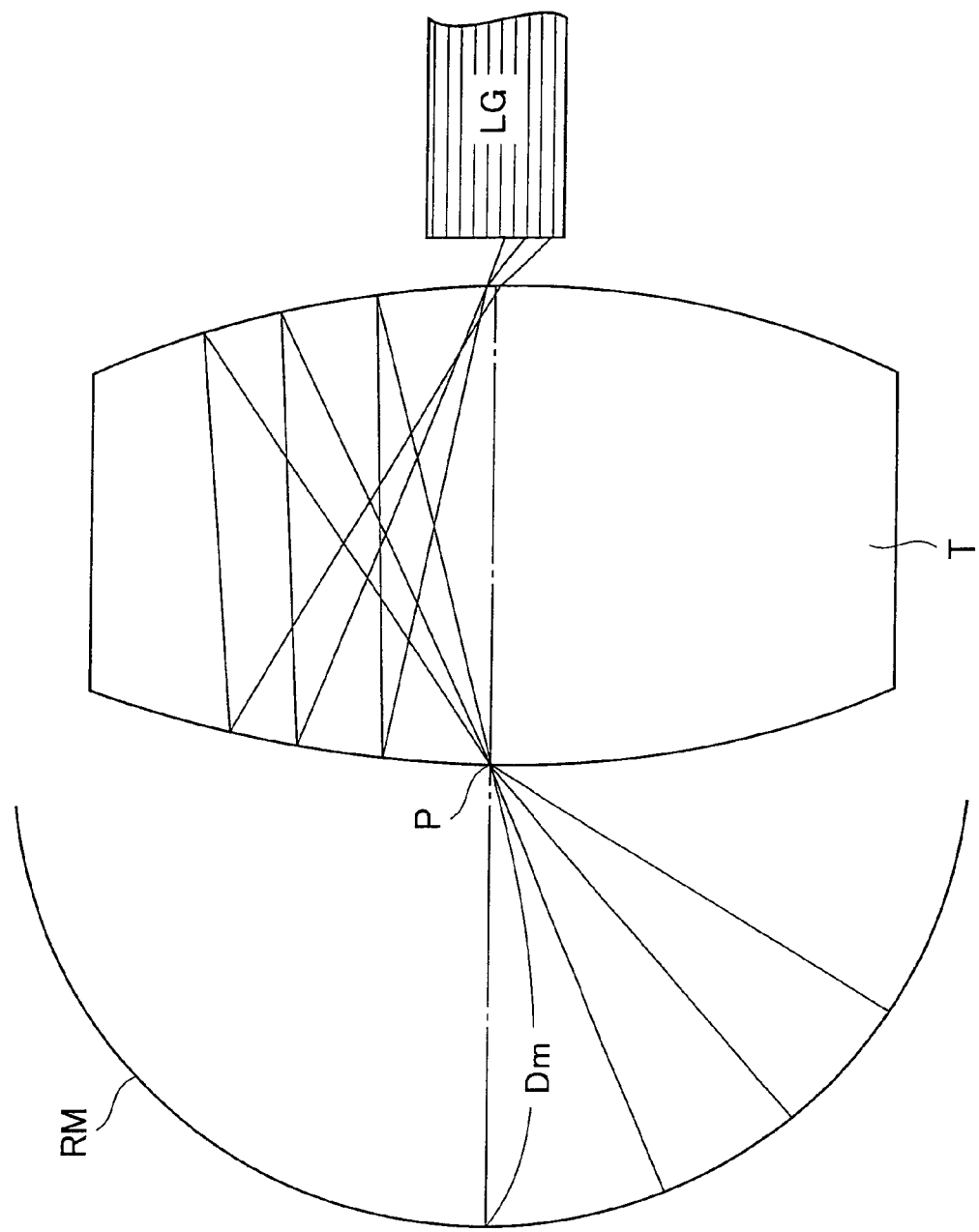
FIG. 13 is a sectional view showing the lens of the light collective optical system of a seventh embodiment in the present invention.

FIG. 13 shows the sectional view of the collective lens of the seventh embodiment. The light source is a xenon light source, and the bright spot of the xenon light source is located at the point P. In the seventh embodiment, a spherical reflecting mirror RM is placed behind the light source (namely, on the opposite side of the collective lens). A distance between the spherical reflecting mirror RM and the bright spot of the light source is equal to the radius of curvature of the spherical reflecting mirror RM. Light diverging backward from the light source is reflected by the spherical reflecting mirror RM so as to turn back toward the point P and is incident on the lens T. On the other hand, light diverging forward from the light source (toward the collective lens side) is incident directly on the lens T. A light beam incident on the lens T follows the same course as in the first to sixth embodiments and enters the light guide LG. By placing the spherical reflecting mirror RM, light can be made efficiently incident on the light guide LG with the least loss of light even in the light source in which light is diffused 360°, such as the xenon light source. In this embodiment, the xenon light source is used, but when such a spherical mirror is provided, a halogen lamp or a mercury vapor lamp may also be used.

In the above embodiments, the range α1 of the first transmissive-refractive surface and the range α2 of the second transmissive-refractive surface are both circular in shape. However, it is needless to say that the shape analogous to the bright spot of the light source allows light to be more efficiently transmitted. In the LED light source, for example, there is the possibility that a light-emitting surface is rectangular, not circular and thus, in this case, it is desirable that the ranges α1 and α2 are both rectangular. Naturally, it is needless to say that the range α1 of the first transmissive-refractive surface larger in size than the bright spot of the light source allows the light of the light source to be more efficiently transmitted.

Eighth Embodiment

Lens data of the eighth embodiment are shown below.
(Light source) d0=0.01
r1=∞ d1=0.8 n'=1.51633 (S-BSL7)
r2=−1.08 (aspherical surface)
K=−0.1
α1=0.1 (dia.), β1=0.0025π, α2=0.8 (dia.), β2=0.16π, Φ=2

$r2/(n'/(-1/d0-(1-n')/r1)-d1/n')=1.99$ (1)

$(1/r1+1/r2)\times r2=1$ (2)

$\beta2/\beta1=64$ (3)

$d1^2/\beta1=64$ (4)

$\Phi^2/\beta1=127.3$ (5)

Figure 14:
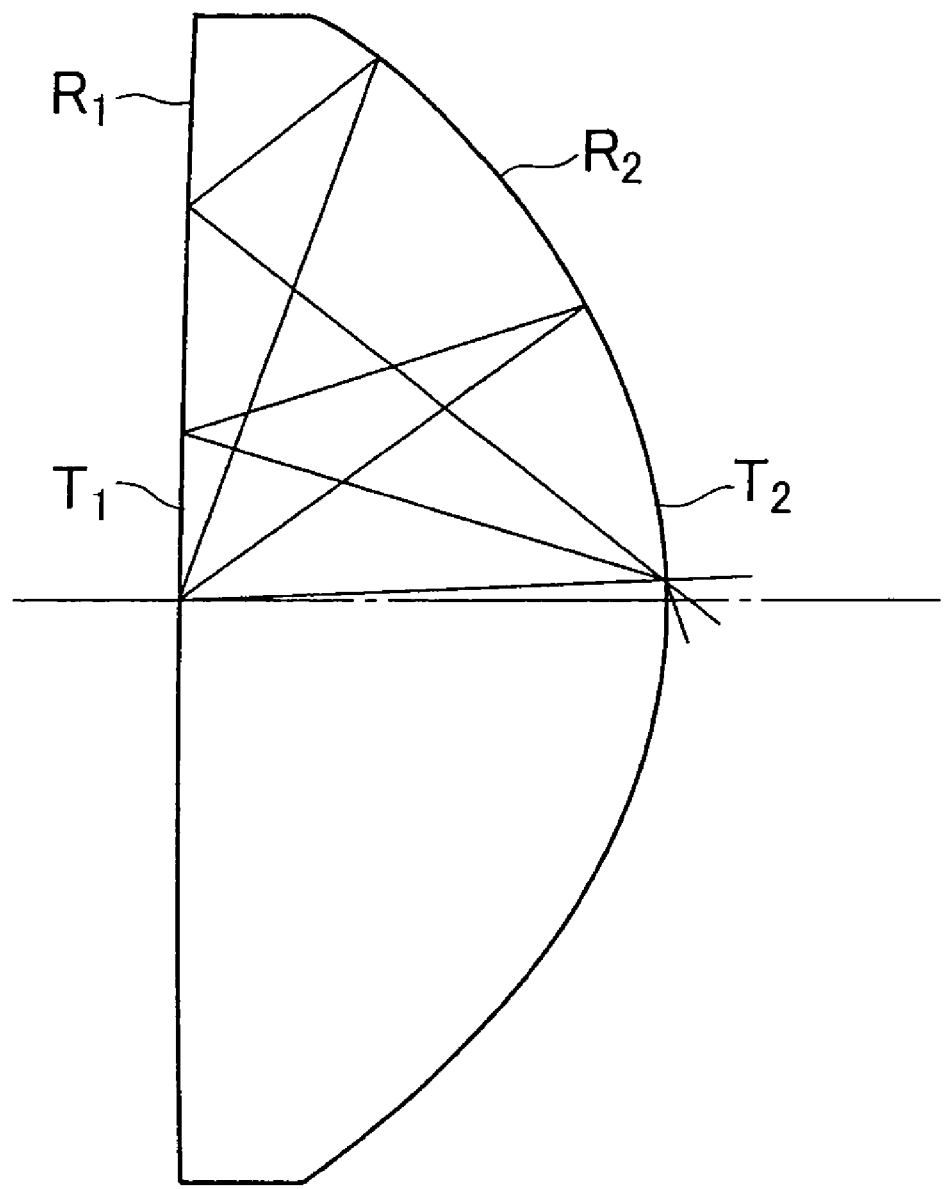
FIG. 14 is a sectional view showing the lens of the light collective optical system of an eighth embodiment in the present invention.

FIG. 14 shows the sectional view of the collective lens of the eighth embodiment. In this embodiment, like the fourth embodiment, the second reflecting surface R2 (the second transmissive-refractive surface T2) is configured as the aspherical surface.

Ninth Embodiment

Lens data of the ninth embodiment are shown below.
(Light source) d0=0
r1=−0.7 d1=0.8 n'=1.51633 (S-BSL7)
r2=−0.915 (aspherical surface)
K=0.035
α1=0.1 (dia.), β1=0.0025π, α2=0.8 (dia.), β2=0.16π, Φ=1.76

$-r2\times n'/d1=1.73$ (1)

$(1/r1+1/r2)\times r2=2.31$ (2)

$\beta2/\beta1=64$ (3)

$d1^2/\beta1=64$ (4)

$\Phi^2/\beta1=98.6$ (5)

Figure 15:
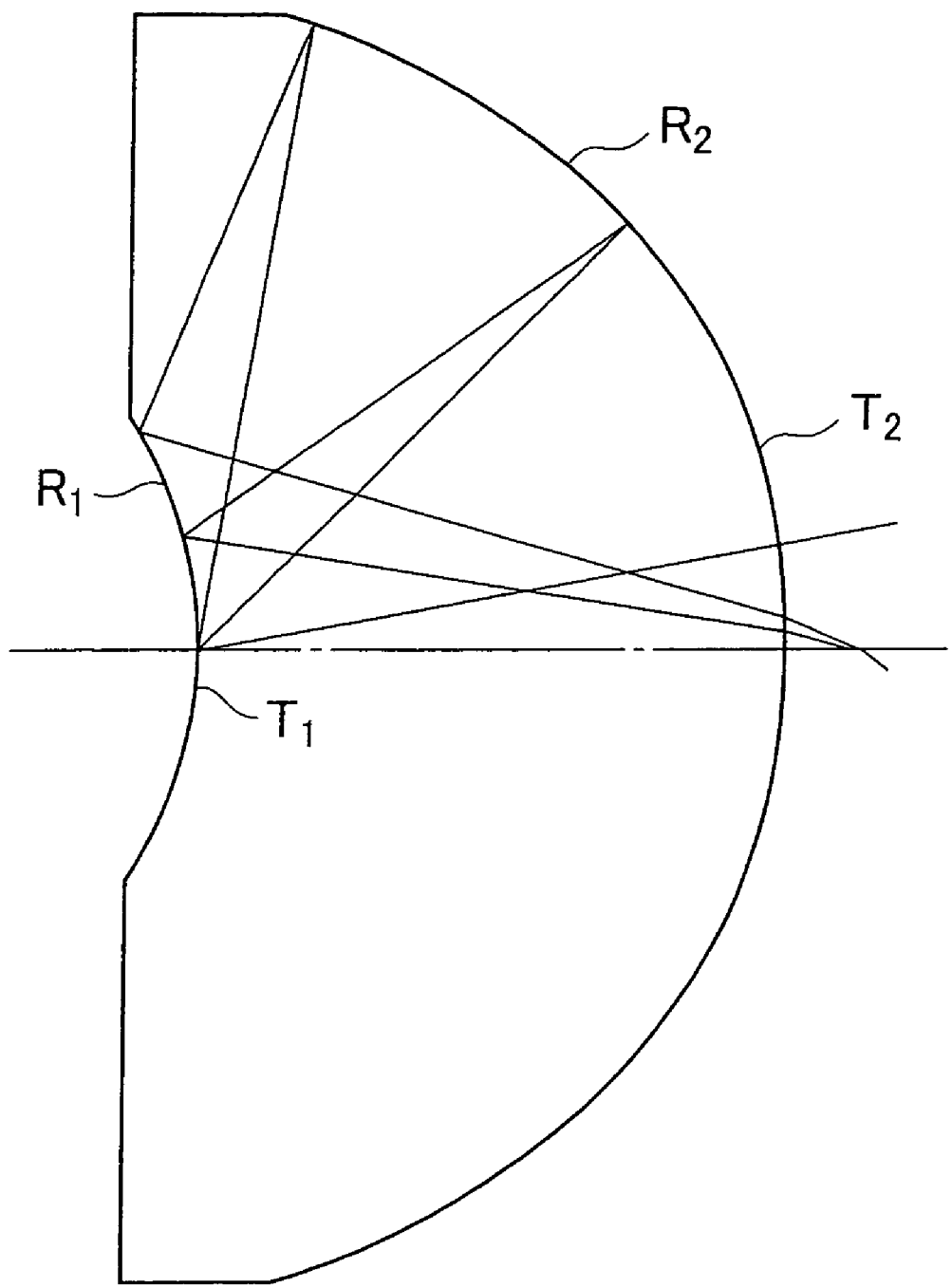
FIG. 15 is a sectional view showing the lens of the light collective optical system of a ninth embodiment in the present invention.

FIG. 15 shows the sectional view of the collective lens of the ninth embodiment. In this embodiment, like the fourth embodiment, the second reflecting surface R2 (the second transmissive-refractive surface T2) is configured as the aspherical surface.

What is claimed is:

1. A light collective optical system comprising, in order from a light source side:
   a first transmissive-refractive surface;
   a second full-mirror surface;
   a first full-mirror surface; and
   a second transmissive-refractive surface,
   which are coaxially arranged along a traveling direction of a light ray.

2. A light collective optical system according to claim 1, wherein the first transmissive-refractive surface and the first full-mirror surface are located on one surface, and the second transmissive-refractive surface and the second full-mirror surface are located on another one surface.

3. A light collective optical system according to claim 1, satisfying the following condition:

$1<r_2/\{n'/[-1/d_0-(1-n')/r_1]-d_1/n'\}$ where when $d_0=0$, $1<-r_2\times n'/d1$; $r_1$ is a radius of curvature of the first full-mirror surface; $r_2$ is a radius of curvature of the second full-mirror surface; n' is a refractive index of a medium, relative to the d line, between the first transmissive-refractive surface and the second transmissive-refractive surface; $d_0$ is a distance from the first transmissive-refractive surface to a bright spot of a light source; and $d_1$ is a coaxial distance between the first full-mirror surface and the second full-mirror surface.

4. A light collective optical system according to claim 3, further satisfying the following condition:

$r^2/\{n'/[-1/d_0-(1-n')/r_1]-d_1/n'\}<3$ where when $d_0=0$, $-r^2\times n'/d1<3$.

5. A light collective optical system according to claim 1, satisfying the following condition:

$0<(1/r1+1/r2)\times r2$ where $r_1$ is a radius of curvature of the first full-mirror surface and $r_2$ is a radius of curvature of the second full-mirror surface.

6. A light collective optical system according to claim 5, further satisfying the following condition:

$(1/r1+1/r2)\times r2<3.$

7. A light collective optical system according to claim 5, further satisfying the following condition:

$$1 < \beta_2/\beta_1$$

where $\beta_1$ is an area of an effective range of the first transmissive-refractive surface and $\beta_2$ is an area of an effective range of the second transmissive-refractive surface.

8. A light collective optical system according to claim 7, further satisfying the following condition:

$$\beta_2/\beta_1 < 80.$$

9. A light collective optical system according to claim 8, further satisfying the following conditions:

$$1 < d_1^2/\beta_1 < 80$$

$$1 < \Phi^2/\beta_1 < 150$$

where $d_1$ is a coaxial distance between the first full-mirror surface and the second full-mirror surface and $\Phi$ is an outer diameter of the first full-mirror surface.

10. A light collective optical system according to claim 1, wherein an effective range of each of the first transmissive-refractive surface and the second transmissive-refractive surface has a shape analogous to a bright spot of a light source.

11. A light collective optical system according to claim 1, wherein an effective range of the first transmissive-refractive surface is larger in size than a bright spot of a light source.

12. A light collective optical system according to claim 1, wherein at least one of the first full-mirror surface and the second full-mirror surface is aspherical.

13. A light collective optical system including a single optical member having a first full-mirror surface and a second full-mirror surface,
wherein a region for the first full-mirror surface is partially replaced by a first transmissive-refractive surface, a region for the second full-mirror surface is partially replaced by a second transmissive-refractive surface, and the first transmissive-refractive surface and the second transmissive-refractive surface are nearly coaxially arranged.

14. A light collective optical system including a single optical member having a first full-mirror surface and a second full-mirror surface,
wherein a region for the first full-mirror surface is partially replaced by a first transmissive-refractive surface, a region for the second full-mirror surface is partially replaced by a second transmissive-refractive surface, the first transmissive-refractive surface is placed in a proximity of a bright spot of a light source, light with a narrow divergence angle from the bright spot of the light source passes through the first transmissive-refractive surface and the second transmissive-refractive surface, and light with a wide divergence angle from the bright spot of the light source travels in order of the first transmissive-refractive surface, the second full-mirror surface, the first full-mirror surface, and the second transmissive-refractive surface so that an image of the bright spot of the light source is projected in a proximity of the second transmissive-refractive surface.

15. A light source device comprising:
a light source;
a light collective optical system including, in order from a light source side:
a first transmissive-refractive surface;
a second full-mirror surface;
a first full-mirror surface; and
a second transmissive-refractive surface,
which are coaxially arranged along a traveling direction of a light ray; and
a spherical reflecting mirror placed behind a bright spot of the light source so that a light beam diverging backward from the bright spot of the light source is reflected back toward the bright spot of the light source.

16. A light source device according to claim 15, wherein the light source is one of a halogen lamp, a xenon lamp, and a mercury vapor lamp.

17. A light source device comprising:
a light source which is a light-emitting diode or a laser diode; and
a light collective optical system including, in order from a light source side:
a first transmissive-refractive surface;
a second full-mirror surface;
a first full-mirror surface; and
a second transmissive-refractive surface,
which are coaxially arranged along a traveling direction of a light ray.

18. A light source device comprising:
a light collective optical system including, in order from a light source side:
a first transmissive-refractive surface;
a second full-mirror surface;
a first full-mirror surface; and
a second transmissive-refractive surface,
which are coaxially arranged along a traveling direction of a light ray; and
a light guide placed in a proximity of a position of image formation of a bright spot of a light source.

* * * * *